US010939827B2

(12) United States Patent
Franz et al.

(10) Patent No.: US 10,939,827 B2
(45) Date of Patent: Mar. 9, 2021

(54) MEASURING APPARATUS FOR THE DETERMINATION OF A TEMPERATURE OF AN OBJECT, THE USE THEREOF AND METHOD FOR THE OPERATION THEREOF, AS WELL AS THERMOTHERAPY DEVICE WITH SUCH A MEASURING APPARATUS

(71) Applicant: Drägerwerk AG & Co. KGaA, Lübeck (DE)

(72) Inventors: Frank Franz, Stockelsdorf (DE); Jochim Koch, Ratzeburg (DE); Ulf Pilz, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 446 days.

(21) Appl. No.: 15/745,214

(22) PCT Filed: Jul. 1, 2016

(86) PCT No.: PCT/EP2016/001133
§ 371 (c)(1),
(2) Date: Jan. 17, 2018

(87) PCT Pub. No.: WO2017/012697
PCT Pub. Date: Jan. 26, 2017

(65) Prior Publication Data
US 2019/0014990 A1 Jan. 17, 2019

(30) Foreign Application Priority Data
Jul. 17, 2015 (DE) .................... 10 2015 009 088.7

(51) Int. Cl.
*A61B 5/01* (2006.01)
*G01J 5/52* (2006.01)
*G01J 5/08* (2006.01)
*A61F 7/00* (2006.01)
*A61N 5/06* (2006.01)
*H04N 5/33* (2006.01)
*G01J 5/00* (2006.01)

(52) U.S. Cl.
CPC ................ *A61B 5/01* (2013.01); *A61F 7/007* (2013.01); *A61N 5/06* (2013.01); *G01J 5/089* (2013.01);
(Continued)

(58) Field of Classification Search
CPC ... A61B 5/01; A61B 2562/0271; A61F 7/007; A61F 2007/0074; A61N 5/06;
(Continued)

(56) References Cited

U.S. PATENT DOCUMENTS 4,407,292 A   10/1983  Edrich
10,110,833 B2 * 10/2018 Teich .................... G01J 5/0846
(Continued)

FOREIGN PATENT DOCUMENTS

CN  1821732 A   8/2006
CN  102374902 A  3/2012
(Continued)

OTHER PUBLICATIONS

Abbas K Abbas et al., Neonatal non-contact respiratory monitoring based on real-time infrared thermography, Biomedical Engineering Online, Biomed Central Ltd, London, GB, Bd. 10, Nr. 1, Oct. 20, 2011 (Oct. 20, 2011), 17 pages.

*Primary Examiner* — Sanjay Cattungal
(74) *Attorney, Agent, or Firm* — McGlew and Tuttle, P.C.

(57) ABSTRACT

A measuring apparatus (1), for the contactless determination of a temperature (T) of an object (100), e.g., of a human, has an infrared camera (10) with a focus (11). A calibrating device (30) is connected to the infrared camera (10) via a data link. The calibrating device (30) has an outer shell (31) with an emissivity on the outside similar to that of the object (100). A temperature sensor (34) is arranged in the outer shell (31). Moreover, a method for contactless determination of a temperature (T) of an object (100) with the measuring
(Continued)

apparatus (1) as well as a method for the operation of the measuring apparatus are provided.

20 Claims, 1 Drawing Sheet

(52) U.S. Cl.
CPC .............. *G01J 5/522* (2013.01); *H04N 5/33* (2013.01); *A61B 2562/0271* (2013.01); *A61F 2007/0074* (2013.01); *A61N 2005/0659* (2013.01); *G01J 2005/0051* (2013.01); *G01J 2005/0077* (2013.01)

(58) Field of Classification Search
CPC .............. A61N 2005/0659; H04N 5/33; G01J 2005/0051; G01J 5/522; G01J 5/089; G01J 2005/0077
See application file for complete search history.

(56) References Cited

U.S. PATENT DOCUMENTS

| | | | |
|---|---|---|---|
| 10,736,551 B2 * | 8/2020 | Rogers | A61B 5/1451 |
| 2005/0110621 A1 * | 5/2005 | Hahn | H04N 7/181 |
| | | | 340/435 |
| 2007/0086506 A1 * | 4/2007 | Dicks | A61B 5/01 |
| | | | 374/121 |
| 2007/0153871 A1 * | 7/2007 | Fraden | G01J 5/0022 |
| | | | 374/121 |
| 2007/0196237 A1 * | 8/2007 | Neuzil | B01L 7/52 |
| | | | 422/67 |
| 2008/0097143 A1 * | 4/2008 | Californniaa | C12M 29/04 |
| | | | 600/22 |
| 2010/0049180 A1 * | 2/2010 | Wells | A61N 5/0616 |
| | | | 606/12 |
| 2010/0198204 A1 * | 8/2010 | Rogers | A61F 7/007 |
| | | | 606/21 |
| 2013/0148688 A1 | 6/2013 | Cao et al. | |
| 2015/0150621 A1 * | 6/2015 | Schwagten | A61B 18/082 |
| | | | 606/31 |
| 2015/0185592 A1 * | 7/2015 | Eineren | G02B 27/0006 |
| | | | 348/375 |

FOREIGN PATENT DOCUMENTS

| | | |
|---|---|---|
| DE | 28 35 602 C2 | 9/1980 |
| DE | 10 2005 049 676 B3 | 11/2006 |
| DE | 10 2013 017911 A1 | 5/2015 |
| EP | 1 221 297 A1 | 7/2002 |
| EP | 1 646 310 B1 | 7/2015 |

\* cited by examiner

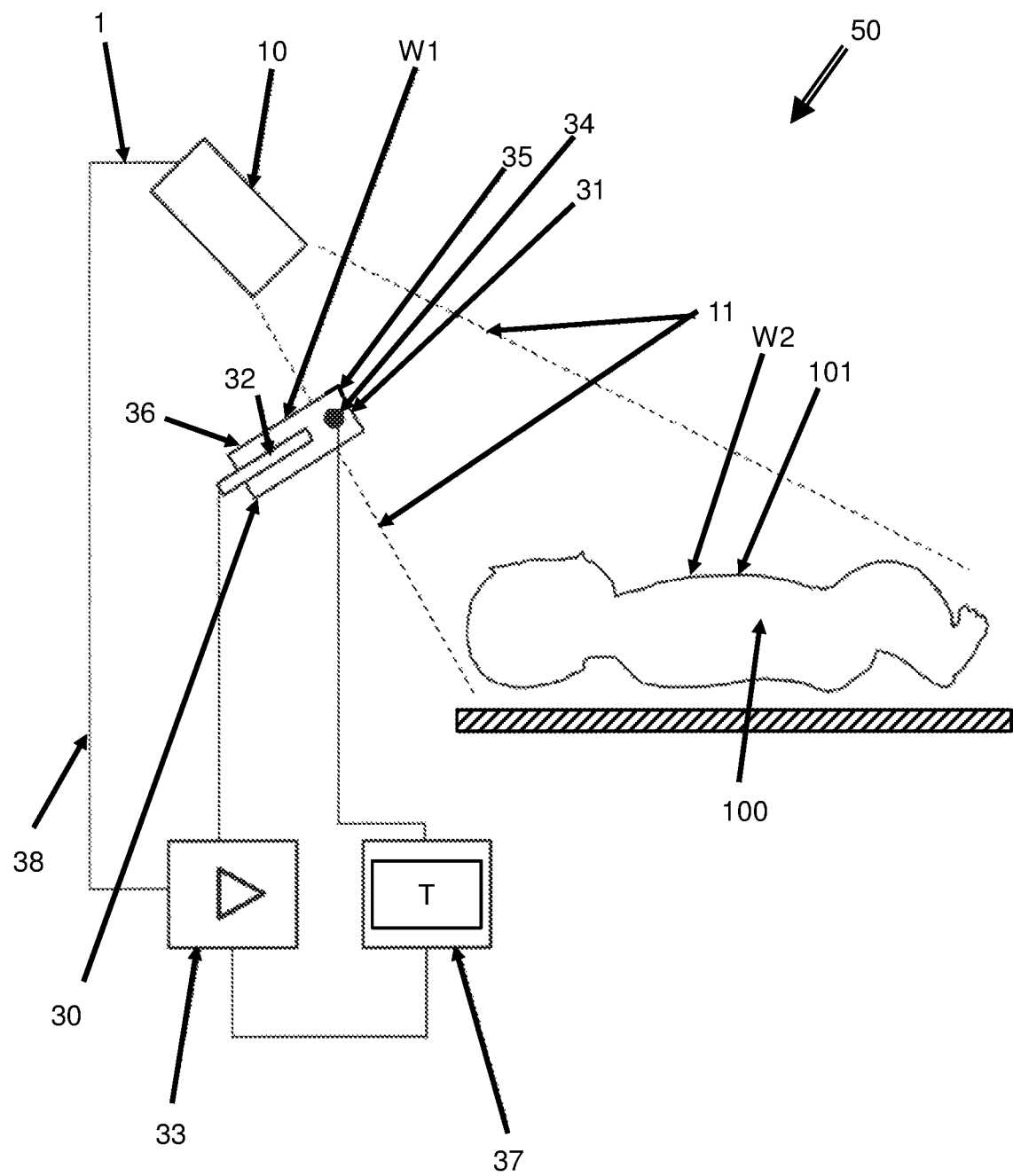

MEASURING APPARATUS FOR THE DETERMINATION OF A TEMPERATURE OF AN OBJECT, THE USE THEREOF AND METHOD FOR THE OPERATION THEREOF, AS WELL AS THERMOTHERAPY DEVICE WITH SUCH A MEASURING APPARATUS

CROSS REFERENCE TO RELATED APPLICATIONS

This application is a United States National Phase Application of International Application PCT/EP2016/001133, filed Jul. 1, 2016, and claims the benefit of priority under 35 U.S.C. § 119 of German Application 10 2015 009 088.7, filed Jul. 17, 2015, the entire contents of which are incorporated herein by reference.

FIELD OF THE INVENTION

The present invention pertains to a measuring apparatus for the determination of a temperature of an object, especially of a body temperature of a living being, and more particularly a body temperature of a human; a thermotherapy device with such a measuring apparatus; the use of such a measuring apparatus; as well as methods, especially for the operation of a measuring apparatus.

BACKGROUND OF THE INVENTION

For a number of reasons, the determination of the temperature of objects is necessary. To this end, a variety of measuring apparatuses and sensors are known from the state of the art.

The determination of the temperature of an object without contacting this object represents a special challenge. Thus, it is described, for example, in DE 10 2005 049 676 B3 how a surface temperature or core temperature of the patient can be determined in a contactless manner by means of an infrared measuring apparatus.

It is problematic that infrared cameras for recording a patient are uncooled and therefore have a low measuring accuracy. In case of the medical body temperature determination, it is required that 95% of all measured values be within ±0.5° C., i.e., the standard deviation between the measuring system and the reference temperature must be less than 0.25° C. However, inexpensive infrared cameras have a standard deviation of >1° C., so that they are unsuitable. Expensive infrared cameras reach a standard deviation of about 0.1° C., but often cannot be purchased for economic reasons.

SUMMARY OF THE INVENTION

An object of the present invention is therefore to provide a measuring apparatus for the contactless determination of a temperature of an object, especially of a body temperature of a living being, and more particularly of a body temperature of a human, which measuring apparatus operates rapidly, achieves a high measuring accuracy in a reliable manner and can be manufactured in a cost-effective manner.

The present invention pertains to a measuring apparatus for the determination of a temperature of an object, especially of a body temperature of a living being, and more particularly a body temperature of a human, having an infrared camera with a focus, wherein a calibrating device is connected to the infrared camera via a data link, wherein the calibrating device has an outer shell with an emissivity on the outside similar to that of the object, wherein a temperature sensor is arranged in the outer shell.

It is advantageous here that measuring inaccuracies of the infrared camera can be compensated by means of the permanently used calibrating device. In case of the optical infrared measurement of a human, the emissivity (also called coefficient of emission) of the skin is not known exactly; however, it is possible to assume a value greater than 0.9 to 0.95 (i.e., a "black body"). When one has the calibrating device in the focus at the same time with the infrared recording of the patient with the infrared camera, a current calibration can be carried out during each temperature determination. It is thus possible to provide a cost-effective measuring apparatus, with which the temperature of an object, especially a body temperature of a living being, and more particularly a body temperature of a human, can be determined rapidly, reliably and with high measuring accuracy.

Using this method, the weakness in the accuracy of inexpensive infrared cameras can therefore be compensated, and a calibration measurement is obtained at all times. The measuring accuracy then essentially depends on the precision of the temperature sensor. Of course, for this purpose the outer shell of the calibrating device shall be able to be arranged in the focus of the infrared camera. The outer shell is optionally connected to the infrared camera with a holding device and is positioned or can be positioned in the focus with the holding device. The outer shell is preferably arranged in the marginal area of the focus. Due to a fixed position in the area of the focus, it is possible to define the image area, in which the outer shell lies, via software. In case of the optional application in a medical incubator, the holding device can be configured, for example, on a hood of the incubator. The infrared camera may also be fixed to the hood.

According to a more specific embodiment of the measuring apparatus, a heating element, which is actuated by a temperature regulator, is arranged in the outer shell, wherein the temperature sensor has a data link to the temperature regulator. It is thus possible, for example, to heat up the outer shell to the same emitted radiation output of the IR radiation as that of the surface region of the object to be measured. A temperature determined with a temperature sensor, for example, with a resistance thermometer, in the outer shell then corresponds to the surface temperature of the object.

In a more specific embodiment of the present invention, which is especially suitable for determining a body temperature of a human, provisions are made for the emissivity on the outside of the outer shell to be similar to the emissivity of human skin, more particularly be between 0.92 and 0.96 and more particularly preferably be between 0.935 and 0.945.

In a special embodiment, the outer shell has a black exterior color (especially a stoving lacquer) on the outside. With such an outer shell, a defined emissivity can be provided on the surface, which emissivity is especially in the range of that of human skin.

Furthermore, a more specific embodiment of the measuring apparatus provides for the outer shell to have a stoving lacquer or an anodized layer on the outside or have a surface structure that generates a similar emissivity. A surface with uniform emissivity can be provided with this manufacturing method.

The outer shell has a metal pipe in one embodiment variant of the measuring apparatus. The pipe shape is suitable for accommodating the temperature sensor and the heating element. The material selection of metal allows a rapid temperature change and thus regulation to a temperature. The determination of the temperature of the object can be carried out correspondingly rapidly. The metal pipe is preferably used as a support element of a coating on the outside, especially of a black exterior color, a stoving lacquer, a special surface structure or an anodized layer.

Moreover, a more specific embodiment provides for the infrared camera to detect infrared radiation in the wavelength range of 8-14 µm, especially the radiation output in this wavelength range. These emission wavelengths in the spectral range of 8 µm to 14 µm typically occur near the ambient temperature of living beings. This spectral range is also called medium and long-wave infrared.

A high precision in the determination of the temperature is achieved in a configuration, according to which the temperature sensor is an NTC (Negative Temperature Coefficient) temperature sensor, a PTC (Positive Temperature Coefficient) temperature sensor, a Pt100 temperature sensor (platinum measuring resistors), a thermocouple or a thermopile consisting of thermocouples.

Platinum measuring resistors are named after their material and after their nominal resistance $R_0$ at a temperature of 0° C. The nominal resistance $R_0=100\Omega$, in a Pt100 temperature sensor.

A thermocouple converts heat into electrical energy by means of thermoelectricity. To this end, two conductors made of different materials are connected electrically to one another. In this connection, a voltage, which depends on the temperature difference between the ends and the contact point, is applied between their ends. Series-connected thermocouples form a thermopile.

In addition, provisions shall be made for the outer shell to be thermally coupled to the temperature sensor and/or to the heating element. As a result of this, the temperature of the surface of the outer shell is changed rapidly. The thermal coupling can take place by direct contact, e.g., by means of precisely fitting insertion of the temperature sensor and/or the heating element into the outer shell. In addition or optionally, possible gaps or cavities can be filled with a fluid or a paste, for example, heat-conducting paste or water.

In a preferred embodiment of the measuring apparatus, the outer shell is arranged closer to the infrared camera than the object. Thus, the outer shell lies in the radius of action of the object or human in a nondisturbing manner.

The measuring apparatus is especially suitable, when it is configured as stationary, for example, via a patient bed or in the area of an identity check, e.g., at airports and in thermotherapy devices (e.g., in medical incubators, warming beds, heat radiators). An automated temperature measurement can then be carried out.

The temperature regulator and a possible analyzer may be arranged in one or more independent housings. They may, however, also be integrated in the housing of the calibrating device or in the housing of the infrared camera.

Furthermore, the present invention pertains to a thermotherapy device with a support for a person, especially a bed or a chair, and with a measuring apparatus as it is described above. With such a device, for example, a medical incubator can be provided, with which the surface temperature of a baby can be measured continuously, in an automated manner, in a contactless manner and precisely as well as optionally also be documented.

The present invention pertains, moreover, to the use of an above-described measuring apparatus for the determination of a temperature, especially a surface temperature, of an object, especially a body temperature of a living being, and more particularly a body temperature of a human.

Due to this use, the temperature of an object, especially a body temperature of a living being, and more particularly a body temperature of a human, can be determined rapidly, reliably and with a high measuring accuracy. In this connection, a cost-effective infrared camera can be used because its measuring inaccuracies can be compensated by means of the permanently inserted calibrating device.

In a more specific form of use, a measuring surface of the object and the outer shell of the calibration device are arranged in the focus of the infrared camera, especially at the same time.

Thus, the radiation output of the emitted wavelength ranges of the outer shell and of the measuring surface can be determined at the same time. In principle, however, it would also be possible to determine the radiation output of the emitted wavelength ranges of the outer shell and of the measuring surface one after the other, i.e., staggered in time. This lasts, as a rule, longer, however, is more uncomfortable and may lead to measuring inaccuracies.

Furthermore, the present invention pertains to a method, especially for the operation of a measuring apparatus described above, in which first a measuring surface of an object and an outer shell of a calibrating device are arranged in the focus of an infrared camera. A determination of the radiation output of the emitted wavelength range of the outer shell and of the radiation output of the emitted wavelength range of the measuring surface is then carried out (especially continuously). During the determination of the radiation output of the wavelength ranges, the temperature in the outer shell is regulated to a value, at which the outer shell emits the radiation output in the same wavelength range as the measuring surface. The temperature, at which the radiation output of the emitted wavelength range of the outer shell is equal to the radiation output of the emitted wavelength range of the measuring surface, is subsequently outputted.

The outputted temperature then corresponds to the surface temperature in the area of the measuring surface of the object. In this connection, the present invention also covers variants, in which the temperature in the outer shell is displayed over the entire time period and finally the temperature, at which the radiation output of the emitted wavelength range of the outer shell is equal to the radiation output of the emitted wavelength range of the measuring surface, is identified visually and/or acoustically as a measurement result, e.g., by means of a continuous rather than blinking display or a beep. It is possible with the method to provide a cost-effective measuring apparatus with a cost-effective infrared camera, with which the temperature of an object, especially a body temperature of a living being, and more particularly a body temperature of a human, can be determined rapidly, reliably and with high measuring accuracy. According to the method, the measuring accuracy is namely essentially dependent on the accuracy of the temperature sensor and not on the accuracy of the infrared camera.

The temperature can be regulated especially by a regulation of the radiation output of the emitted wavelength range of the outer shell to the value of the radiation output of the emitted wavelength range of the measuring surface by the temperature of the outer shell being changed.

The present invention further pertains to a method, especially for the operation of a measuring apparatus described above, in which first a measuring surface of an object and an outer shell of a calibrating device are arranged in the focus of an infrared camera. A determination of the radiation output of the emitted wavelength range of the outer shell and of the radiation output of the emitted wavelength range of the measuring surface is then carried out. In addition, the temperature of the outer shell is determined. A correction factor based on the relationship between the temperature of the outer shell and the radiation output of the determined emitted wavelength range of the outer shell is then determined. Subsequently, a temperature is associated with the determined radiation output of the emitted wavelength range of the measuring surface, taking the determined correction factor into consideration, which temperature is then outputted.

An advantage of the method is that the temperature determined at the object is corrected by means of the correction factor, which is always determined currently and contains the current measuring deviation. Slight inaccuracies due to different emissivity and the actual core temperatures of the object and of the outer shell each, are negligible, especially markedly lower than temperatures of the object determined without a correction factor.

According to an optional addition to the method, the temperature of the outer shell is regulated to a defined value, and the correction factor is determined based on the relationship between the defined value and the radiation output of the determined emitted wavelength range of the outer shell.

The regulation to a defined temperature has the advantage that markedly more precise temperature measurements are possible even in the case of unknown or variable ambient temperatures. The regulation may be started already before the actual determination of the temperature. The actual temperature measurement of the object can then be carried out very rapidly because hardly any inertia occurs as to the temperature changes of the outer shell, for which it would be necessary to wait.

The defined value to which the temperature in the outer shell is optionally regulated shall preferably correspond to approximately the expected temperature of the object. For example, the outer shell is optionally regulated between 37° C. and 39° C. for measuring the temperature of a human. At constant ambient temperatures, such as in laboratories or other temperature-controlled rooms, the regulation can also be implemented by external temperature control. A good compensation of measuring inaccuracies of the infrared camera can also already be achieved when the outer shell assumes the then present ambient temperature. In case of inconstant ambient temperatures, a temperature control of the outer shell to a temperature between 25° C. and 30° C. is also sufficient for a good compensation.

Further features, details and advantages of the present invention appear from the text of the claims as well as from the following description of an exemplary embodiment on the basis of the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of a thermotherapy device having a measuring apparatus with an infrared camera, in the focus of which an object is located.

DESCRIPTION OF THE PREFERRED EMBODIMENTS

Referring to the drawings, FIG. 1 shows a schematic view of a thermotherapy device 50 having a measuring apparatus 1 for the determination of a temperature T of an object 100. In the present case, this object is a human, whose body temperature shall be determined, namely a baby in a medical incubator.

The measuring apparatus has an infrared camera 10 with a focus 11, which infrared camera detects the radiation output of infrared radiation in the wavelength range of 8-14 µm. The object 100 and an outer shell 31 of a calibrating device 30 are arranged in the focus 11. It is seen that the outer shell 31 is arranged closer to the infrared camera 10 than the object 100. A stationary configuration of the measuring apparatus 1 over a patient bed for small children is shown by way of example.

The calibrating device 30 is connected to the infrared camera 10 via a data link 38. Furthermore, the calibrating device 30 is equipped with the outer shell 31, which has an emissivity on the outside similar to that of the object 100. The emissivity on the outside of the outer shell 31 is similar to the emissivity of human skin and is between 0.92 and 0.96, preferably between 0.935 and 0.945. In this case, the outer shell 31 has a metal pipe 35, which carries a coating 36 on the outside, which coating has especially a black exterior color. Such a coating can be formed, for example, by a stoving lacquer or an anodized layer.

A heating element 32, which is actuated by a temperature regulator 33, is arranged in the outer shell 31 of the calibrating device 30. In addition, a temperature sensor 34, which has a data link to the temperature regulator 33, is located in the outer shell 31. The temperature sensor 34 is, in addition, connected to a display device 37, especially to a display, for outputting the temperature T. The temperature sensor 34 may be an NTC (Negative Temperature Coefficient) temperature sensor, a PTC (Positive Temperature Coefficient) temperature sensor, a Pt100 temperature sensor (platinum measuring resistors), a thermocouple or a thermopile consisting of thermocouples.

Such a measuring apparatus 1 can be used to determine the temperature T of the object 100. To this end, a measuring surface 101 of the object 100, which points in the direction of the infrared camera 10, and the outer shell of the calibrating device 30 are arranged in the focus 11 of the infrared camera 10. The measuring surface emits a wavelength range W2 and the outer shell 31 emits a wavelength range W1.

A method, in which the following steps are carried out, can now be carried out with such a measuring apparatus:

a) Arrangement of a measuring surface 101 of an object 100 and of the outer shell 31 of the calibrating device 30 in the focus 11 of the infrared camera 10;

b) continuous determination of the radiation output of the emitted wavelength range W1 of the outer shell 31 and of the radiation output of the emitted wavelength range W2 of the measuring surface 101;

c) regulation of the temperature T in the outer shell 31 to a value, at which the outer shell 31 emits the same radiation output in the wavelength range W1, W2 as the measuring surface 101, and especially by regulation of the radiation output of the emitted wavelength range W1 of the outer shell 31 to the value of the radiation output of the emitted wavelength range W2 of the measuring surface 101 by the temperature T in the outer shell 31 being changed; and d) output of the temperature T, at which the radiation output of the emitted wavelength range W1 of the outer shell 31 is identical to the radiation output of the emitted wavelength range W2 of the measuring surface 101.

The outputted temperature T then corresponds to the core temperature in the area of the measuring surface 101 of the object 100.

A method, in which the following steps are carried out, may optionally also be carried out with such a measuring apparatus:

a) Arrangement of the measuring surface 101 of the object 100 and of the outer shell 31 of the calibrating device 30 in the focus 11 of an infrared camera 10;
b) determination of the radiation output of the emitted wavelength range W1 of the outer shell 31 and of the radiation output of the emitted wavelength range W2 of the measuring surface 101;
c) determination of a temperature of the outer shell 31;
d) determination of a correction factor based on the determined radiation output of the emitted wavelength range W1 of the outer shell 31 and determination of the correction factor based on the relationship between the temperature of the outer shell (31) and the determined radiation output of the emitted wavelength range W1 of the outer shell 31;
e) association of a temperature T with the determined radiation output of the emitted wavelength range W2 of the measuring surface 101, taking the determined correction factor into consideration; and
f) output of the temperature T.

The method may optionally be complemented by the following steps being carried out:

Regulation of the temperature of the outer shell (31) to a defined value in step c); and determination of the correction factor based on the relationship between the defined value and the radiation output of the determined emitted wavelength range (W1) of the outer shell (31) in step d).

The present invention is not limited to one of the above-described embodiments, but rather can be modified in a variety of ways.

All features and advantages, including design details, arrangements in space and method steps appearing from the claims, the specification and the drawing, may be essential to the present invention both in themselves and in the widest variety of combinations.

While specific embodiments of the invention have been shown and described in detail to illustrate the application of the principles of the invention, it will be understood that the invention may be embodied otherwise without departing from such principles.

The invention claimed is:

1. A measuring apparatus for the determination of a temperature of an object comprising a body temperature of a living being, the measuring apparatus comprising:
an infrared camera with an infrared camera focus;
a calibrating device connected to the infrared camera via a data link, wherein the calibrating device has an outer shell with an emissivity on the outside similar to that of the object; and
a temperature sensor arranged in the outer shell, the calibrating device being configured to determine a correction factor based on a relationship between a temperature of the outer shell and a radiation output of a determined emitted wavelength range of the outer shell and the calibrating device being configured to associate a temperature with the determined radiation output of the emitted wavelength range of a measuring surface of the object, taking the determined correction factor into consideration.

2. A measuring apparatus in accordance with claim 1, further comprising:
a temperature regulator; and
a heating element, which is actuated by the temperature regulator arranged in the outer shell, wherein the temperature sensor has a data link to the temperature regulator.

3. A measuring apparatus in accordance with claim 1, wherein the emissivity on the outside of the outer shell being similar to that of the object comprises the emissivity on the outside of the outer shell being similar to the emissivity of human skin.

4. A measuring apparatus in accordance with claim 3, wherein the emissivity on the outside of the outer shell is between 0.92 and 0.96.

5. A measuring apparatus in accordance with claim 3, wherein the emissivity on the outside of the outer shell is between 0.935 and 0.945.

6. A method in accordance with claim 4, wherein the object is a person and the emissivity on the outside of the outer shell being similar to that of the object comprises the emissivity on the outside of the outer shell being similar to the emissivity of human skin and being between 0.92 and 0.96.

7. A measuring apparatus in accordance with claim 1, wherein the outer shell has a black exterior color on an outside thereof.

8. A measuring apparatus in accordance with claim 1, wherein the outer shell has a stoving lacquer or an anodized layer on an outside thereof.

9. A measuring apparatus in accordance with claim 1, wherein the outer shell comprises a metal pipe.

10. A measuring apparatus in accordance with claim 1, wherein the infrared camera detects infrared radiation in the wavelength range of 8-14 μm.

11. A measuring apparatus in accordance with claim 1, wherein the temperature sensor is an NTC (Negative Temperature Coefficient) temperature sensor, a PTC (Positive Temperature Coefficient) temperature sensor, a Pt100 temperature sensor (platinum measuring resistors), a thermocouple or a thermopile consisting of thermocouples.

12. A thermotherapy device comprising:
a support for a person;
a measuring apparatus comprising:
an infrared camera with an infrared camera focus;
a calibrating device connected to the infrared camera via a data link, wherein the calibrating device has an outer shell with an emissivity on the outside similar to that of the person; and
a temperature sensor arranged in the outer shell, the calibrating device being configured to determine a correction factor based on a relationship between a temperature of the outer shell and a radiation output of a determined emitted wavelength range of the outer shell and the calibrating device being configured to associate a temperature with a determined radiation output of an emitted wavelength range of a measuring surface of the person, taking the determined correction factor into consideration.

13. A thermotherapy device in accordance with claim 12, further comprising:
a temperature regulator; and
a heating element, which is actuated by the temperature regulator, arranged in the outer shell, wherein the temperature sensor has a data link to the temperature regulator.

14. A thermotherapy device in accordance with claim 12, wherein the emissivity on the outside of the outer shell being similar to that of the person comprises the emissivity on the outside of the outer shell being similar to the emissivity of human skin and being between 0.92 and 0.96.

15. A method for the determination of a temperature of an object, the method comprising the steps of:
providing a measuring apparatus comprising an infrared camera with an infrared camera focus, a calibrating device connected to the infrared camera via a data link, wherein the calibrating device has an outer shell with an emissivity on the outside similar to that of the person, and a temperature sensor arranged in the outer shell;
positioning the object relative to the measuring apparatus;
determining a correction factor based on a relationship between a temperature of the outer shell and a radiation output of a determined emitted wavelength range of the outer shell;
associating a temperature with the determined radiation output of an emitted wavelength range of a measuring surface of the object, taking the determined correction factor into consideration;
measuring the body temperature of the person with the measuring apparatus.

16. A method in accordance with claim 15, further comprising:
arranging a measuring surface of the object in the infrared camera focus of the infrared camera as part of the step of positioning;
arranging the outer shell of the calibrating device in the infrared camera focus of the infrared camera;
determining the radiation output of the emitted wavelength range of the outer shell and of the radiation output of the emitted wavelength range of the measuring surface as part of the step of measuring;
regulating the temperature of the outer shell to a value, at which the outer shell emits the same radiation output in the wavelength range as the measuring surface as part of the step of measuring; and
outputting the temperature, at which the radiation output of the emitted wavelength range of the outer shell is identical to the radiation output of the emitted wavelength range of the measuring surface as part of the step of measuring.

17. A method in accordance with claim 16, wherein:
a temperature regulator is provided; and
a heating element is actuated by the temperature regulator, arranged in the outer shell, wherein the temperature sensor has a data link to the temperature regulator for the regulating of the temperature of the outer shell.

18. A method in accordance with claim 17, wherein the emissivity on the outside of the outer shell being similar to that of the person comprises the emissivity on the outside of the outer shell being similar to the emissivity of human skin and being between 0.92 and 0.96.

19. A method for the operation of a measuring apparatus the method comprising the steps of:
providing a measuring apparatus comprising an infrared camera with an infrared camera focus, a calibrating device connected to the infrared camera via a data link, wherein the calibrating device has an outer shell with an emissivity on the outside similar to that of an object, and a temperature sensor arranged in the outer shell;
arranging a measuring surface of the object and of an outer shell of the calibrating device in the infrared camera focus of the infrared camera;
determining radiation output of the emitted wavelength range of the outer shell and of the emitted wavelength range of the measuring surface;
determining a temperature of the outer shell;
determining a correction factor based on the relationship between the temperature of the outer shell and the radiation output of the determined emitted wavelength range of the outer shell;
associating a temperature with the determined radiation output of the emitted wavelength range of the measuring surface, taking the determined correction factor into consideration; and
outputting the temperature.

20. A method in accordance with claim 19, further comprising the steps of:
regulating the temperature of the outer shell to a defined value;
determining the correction factor based on the relationship between the defined value and the radiation output of the determined emitted wavelength range of the outer shell.

* * * * *